United States Patent
McNamara et al.

(10) Patent No.: US 8,439,964 B2
(45) Date of Patent: May 14, 2013

(54) STENT WITH WEB-INDUCING NODES FOR INCREASED SURFACE AREA

(75) Inventors: Adrian McNamara, Newcastle (IE); David McMorrow, Fort Lorenzo (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1577 days.

(21) Appl. No.: 11/211,106

(22) Filed: Aug. 23, 2005

(65) Prior Publication Data

US 2007/0055366 A1 Mar. 8, 2007

(51) Int. Cl.
*A61F 2/06* (2006.01)
(52) U.S. Cl.
USPC .......................... 623/1.15; 623/1.42
(58) Field of Classification Search ................... 623/1.15
See application file for complete search history.

(56) References Cited

U.S. PATENT DOCUMENTS

| | | | |
|---|---|---|---|
| 5,662,713 A | 9/1997 | Andersen et al. | |
| 5,968,091 A * | 10/1999 | Pinchuk et al. | 427/2.24 |
| 6,120,847 A * | 9/2000 | Yang et al. | 427/335 |
| 6,254,632 B1 | 7/2001 | Wu et al. | |
| 6,379,379 B1 | 4/2002 | Wang | |
| 6,533,807 B2 | 3/2003 | Wolinsky et al. | |
| 6,562,063 B1 | 5/2003 | Euteneuer et al. | |
| 6,565,659 B1 | 5/2003 | Pacetti et al. | |
| 6,613,079 B1 | 9/2003 | Wolinsky et al. | |
| 7,208,190 B2 | 4/2007 | Verlee et al. | |
| 7,390,525 B2 | 6/2008 | Epstein et al. | |
| 7,491,234 B2 | 2/2009 | Palasis et al. | |
| 2002/0116050 A1* | 8/2002 | Kocur | 623/1.15 |
| 2002/0161428 A1* | 10/2002 | Oepen et al. | 623/1.15 |
| 2003/0088307 A1 | 5/2003 | Shulze | |
| 2003/0139798 A1 | 7/2003 | Brown et al. | |
| 2003/0144727 A1 | 7/2003 | Rosenthal | |
| 2004/0024448 A1* | 2/2004 | Chang et al. | 623/1.42 |
| 2005/0004654 A1* | 1/2005 | Khosravi et al. | 623/1.13 |
| 2007/0009565 A1* | 1/2007 | Pacetti et al. | 424/423 |

FOREIGN PATENT DOCUMENTS

WO 2004/037443 5/2004

OTHER PUBLICATIONS

Hackworth et al., Development and First Application o Bistable Expandable Sand Screen, Society of Petroleum Engineers Inc., Copyright 2003.

* cited by examiner

*Primary Examiner* — Thomas J Sweet
*Assistant Examiner* — Matthew Schall
(74) *Attorney, Agent, or Firm* — Vidas, Arrett & Steinkraus, P.A.

(57) ABSTRACT

A medical device for delivering a therapeutic agent is described comprising a stent comprising a sidewall and a plurality of struts, wherein at least one strut or strut portion comprises at least one node, wherein the expansion of the stent creates at least one web comprising a coating composition having a therapeutic agent, and wherein at least one node is configured to be associated with at least one web. A method for delivering a therapeutic agent to a body site is also described.

28 Claims, 13 Drawing Sheets

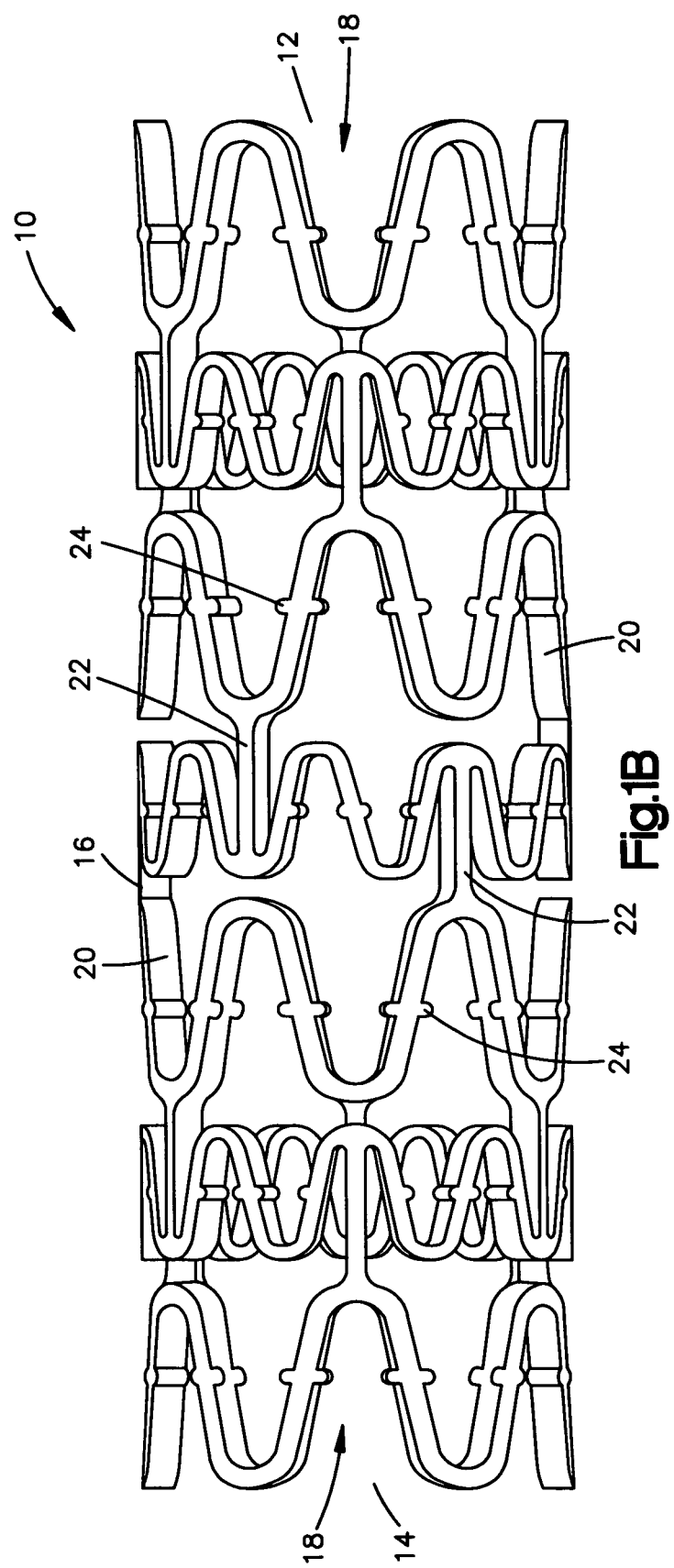

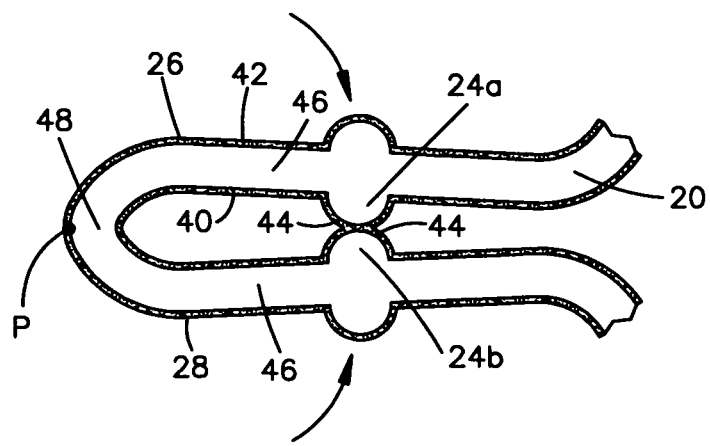
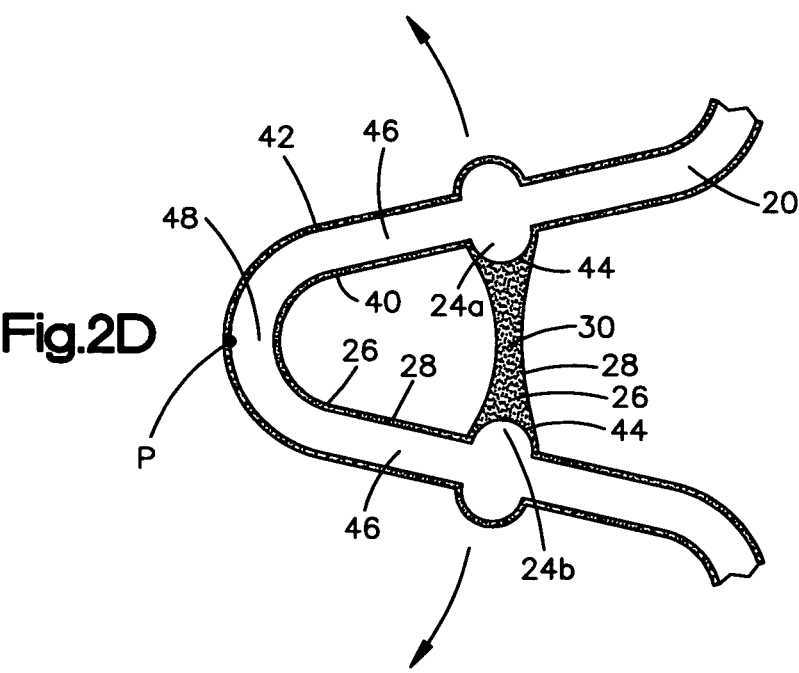

STENT WITH WEB-INDUCING NODES FOR INCREASED SURFACE AREA

FIELD OF THE INVENTION

This invention relates generally to medical devices, such as stents, for delivering a therapeutic agent to body tissue of a patient, such as a body lumen. More particularly, the invention is directed to a stent comprising web-inducing nodes for increasing the stent surface area used to deliver a therapeutic agent. The invention is also directed to a method for delivering a therapeutic agent to body tissue of a patient.

BACKGROUND OF THE INVENTION

A variety of medical conditions have been treated by introducing an insertable medical device having a coating for release of a therapeutic agent. For example, various types of medical devices coated with a therapeutic agent, such as stents, have been proposed for localized delivery of such agents to a body lumen. See, e.g., U.S. Pat. No. 6,099,562 to Ding et al. issued on Aug. 8, 2000. However, it has been noted that therapeutic agent delivery by means of medical devices can be improved.

In particular, the effectiveness of coated medical devices is limited by the surface area of the medical device. This problem is exacerbated when the medical device is used to delivery biopharmaceuticals, such as gene therapies and proteins. Generally, biopharmaceuticals have large therapeutic application windows. The use of coated medical devices makes the upper areas of these windows difficult or impossible to explore and test because of the limited carrying capacity of a coated medical device. The present invention provides a medical device that has increased carrying capacity to address this and other needs.

It is therefore an objective of the present invention to allow for increased therapeutic agent elution capabilities while still preserving the benefits of expandable medical devices.

SUMMARY OF THE INVENTION

A method for delivering a therapeutic agent to a body site is described comprising the steps of: (a) providing a stent comprising a sidewall and a plurality of struts; wherein at least a first strut has at least a first node on a first portion of the first strut; (b) coating at least the first node with a coating composition comprising at least one therapeutic agent; (c) compressing the stent; (d) implanting the stent in the body of a patient; and (e) expanding the stent within the body; wherein the expansion of the stent creates at least a first web of coating composition which extends from the first node to a second portion of the first strut.

The second portion may comprise at least a second node and the first web may extend between the first node and the second node. The first node may be substantially rounded, substantially triangular, or substantially rectangular. The first node and the second node may be substantially the same shape and/or substantially the same size.

The method may further comprise coating the second node with a coating composition comprising at least one therapeutic agent. A substantial portion of the stent may be coated.

The first portion may comprise a second node and the second portion comprises a third node and a fourth node, and wherein the first web extends between the first node and the third node, and a second web extends between the second node and the fourth node. The first web and the second web may be different shapes. The first node and the second node may be substantially a first shape, wherein the third node and the fourth node may be substantially a second shape, and wherein the first shape may be substantially different than the second shape. The first node and the second node may be substantially a first size, wherein the third node and the fourth node may be substantially a second size, and wherein the first shape may be larger than the second size.

The first portion may comprise a first plurality of nodes and the second portion may comprise a second plurality of nodes, wherein a plurality of webs may extend between the first plurality of nodes and the second plurality of nodes. The first portion may comprise a first anti-node substantially aligned with the first node.

Another method for delivering a therapeutic agent to a body site is described, comprising the steps of: (a) providing a stent comprising a sidewall and a plurality of struts; wherein at least a first strut has at least a first node; (b) coating at least the first node with a coating composition comprising at least one therapeutic agent; (c) compressing the stent; (d) implanting the stent in the body of a patient; and (e) expanding the stent within the body; wherein the expansion of the stent creates at least a first web of coating composition which extends from the first node to a second strut.

A medical device for delivering a therapeutic agent is also described, comprising: a stent comprising a sidewall and a plurality of struts, wherein at least a first strut comprises at least a first node on a first portion of the strut; a coating composition comprising a therapeutic agent disposed on the first node; and at least a first web comprising the coating composition which extends from the first node to a second position of the strut.

The second portion may comprise at least a second node, wherein the first web extends between the first node and the second node.

Another medical device for delivering a therapeutic agent is described, comprising: a stent comprising a sidewall and a plurality of struts, wherein at least a first strut comprises a first node; a coating composition comprising a therapeutic agent disposed on the first node; and at least a first web comprising the coating composition which extends from the first node to a second strut.

BRIEF DESCRIPTION OF THE DRAWINGS

Preferred features of the present invention are disclosed in the accompanying drawings, wherein similar reference characters denote similar elements throughout the several views, and wherein:

FIG. 1B is a side view of the stent of FIG. 1A;

FIG. 2C shows the strut of FIG. 2B in a compressed condition;

FIG. 2D shows the strut of FIG. 2C in an expanded condition, with a resulting web;

DETAILED DESCRIPTION OF THE INVENTION

Figure 1A:
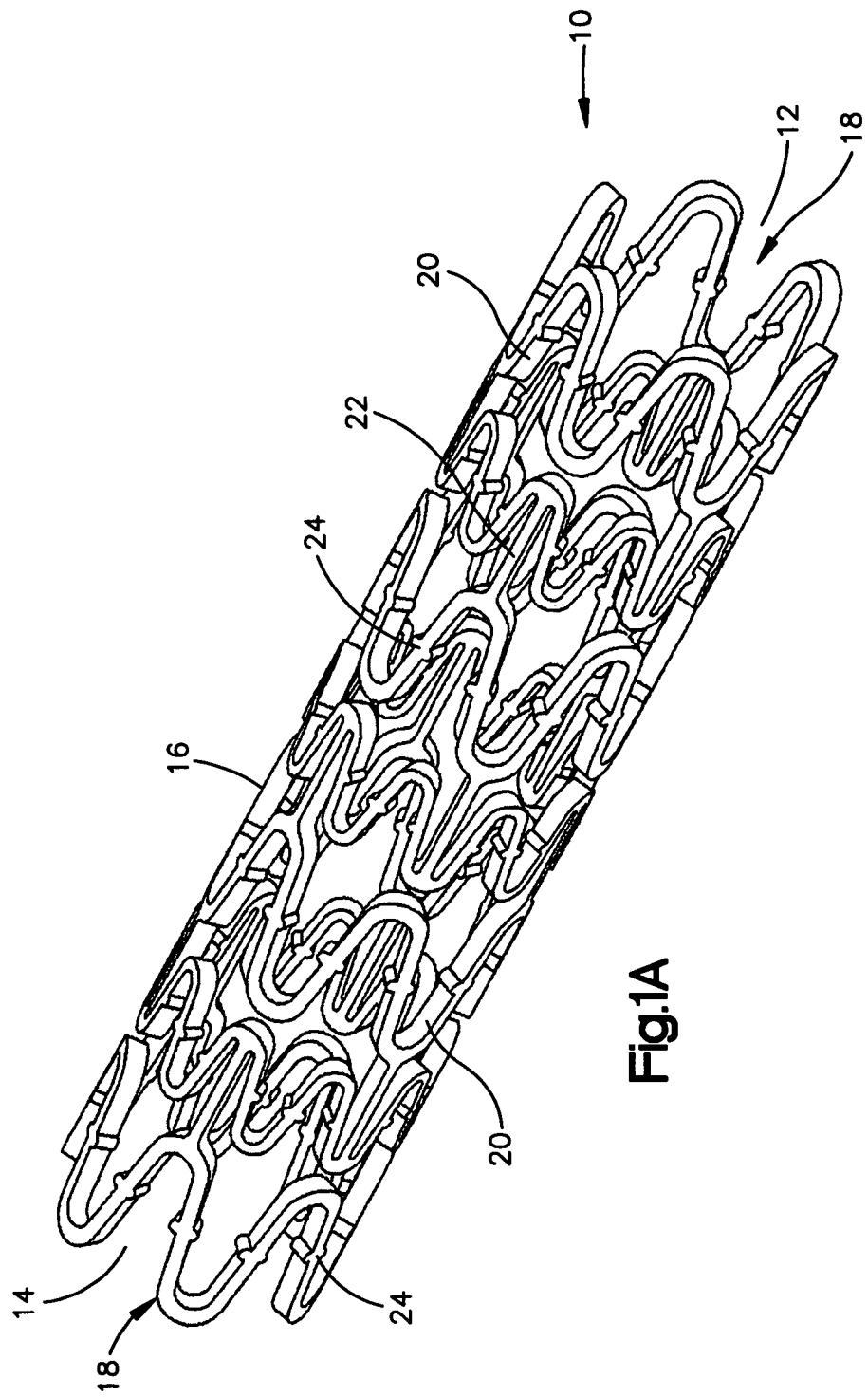
FIG. 1A is a perspective view of an exemplary stent with web-inducing nodes.

The invention described in detail herein generally relates to a stent having at a strut having at least one web-inducing node, i.e. nodes. Suitable stents include ones that are used for cardiovascular, urinary and other medical applications. FIG. 1A shows an example of a stent suitable for the present invention. In this example, the stent 10 comprises a sidewall 16 which comprises a plurality of struts 20. Stent 10 may have a first end 12 and a second end 14. Stent 10 may also have a flow path 18 passing therethrough. Struts 20 may be connected by connecting elements 22. Also, the sidewall 16 may have a first sidewall surface and an opposing second sidewall surface, which are not shown in FIG. 1A. The first sidewall surface can be an outer sidewall surface, which faces the body lumen wall when the stent is implanted, or an inner sidewall surface, which faces away from the body lumen wall. Likewise, the second sidewall surface can be an outer sidewall surface or an inner sidewall surface.

FIG. 1A also shows a stent 10 having web-inducing nodes 24 located on struts 20. As discussed in more detail below, the nodes 24 may be of a variety of shapes, sizes, and locations. Moreover, a single strut 20 may have a single node 24, two nodes 24, or any suitable number of nodes 24. Similarly, a single stent 10 may comprise one or numerous struts 20 having nodes 24. The characteristics of nodes 24 may vary from strut to strut 20. Again, a more detailed discussion of nodes 24 appears supra.

FIG. 1B is a side view of the stent 10 of FIG. 1A. As seen clearly in this embodiment, the characteristics of struts 20 themselves may vary in a single stent 10.

Other suitable stents include, for example, intravascular stents such as those described in U.S. Pat. No. 6,478,816 to Kveen et al., for "Stent", issued on Nov. 12, 2002, incorporated herein by reference in its entirety. Suitable stents include self-expanding stents and balloon expandable stents. Examples of self-expanding stents useful in the present invention are illustrated in U.S. Pat. Nos. 4,655,771 and 4,954,126 issued to Wallsten and U.S. Pat. No. 5,061,275 issued to Wallsten et al. Examples of appropriate balloon-expandable stents are shown in U.S. Pat. No. 5,449,373 issued to Pinchasik et al.

Stents that are suitable for the present invention may be fabricated from metallic, ceramic, or polymeric materials, or a combination thereof. Metallic materials are more preferable. Suitable metallic materials include metals and alloys based on titanium (such as nitinol, nickel titanium alloys, thermo-memory alloy materials), stainless steel, tantalum, nickel-chrome, or certain cobalt alloys including cobalt-chromium-nickel alloys such as Elgiloy® and Phynox®. Metallic materials also include clad composite filaments, such as those disclosed in WO 94/16646.

Suitable ceramic materials include, but are not limited to, oxides, carbides, or nitrides of the transition elements such as titaniumoxides, hafnium oxides, iridiumoxides, chromium oxides, aluminum oxides, and zirconiumoxides. Silicon based materials, such as silica, may also be used.

The polymer(s) useful for forming the stent should be ones that are biocompatible and avoid irritation to body tissue. They can be either biostable or bioabsorbable. Suitable polymeric materials include without limitation polyurethane and its copolymers, silicone and its copolymers, ethylene vinyl-acetate, polyethylene terephtalate, thermoplastic elastomers, polyvinyl chloride, polyolefins, cellulosics, polyamides, polyesters, polysulfones, polytetrafluorethylenes, polycarbonates, acrylonitrile butadiene styrene copolymers, acrylics, polylactic acid, polyglycolic acid, polycaprolactone, polylactic acid-polyethylene oxide copolymers, cellulose, collagens, and chitins.

Other polymers that are useful as materials for stents include without limitation dacron polyester, poly(ethylene terephthalate), polycarbonate, polymethylmethacrylate, polypropylene, polyalkylene oxalates, polyvinylchloride, polyurethanes, polysiloxanes, nylons, poly(dimethyl siloxane), polycyanoacrylates, polyphosphazenes, poly(amino acids), ethylene glycol I dimethacrylate, poly(methyl methacrylate), poly(2-hydroxyethyl methacrylate), polytetrafluoroethylene poly(HEMA), polyhydroxyalkanoates, polytetrafluorethylene, polycarbonate, poly(glycolide-lactide) co-polymer, polylactic acid, poly(γ-caprolactone), poly(γ-hydroxybutyrate), polydioxanone, poly(γ-ethyl glutamate), polyiminocarbonates, poly(ortho ester), polyanhydrides, alginate, dextran, chitin, cotton, polyglycolic acid, polyurethane, or derivatized versions thereof, i.e., polymers which have been modified to include, for example, attachment sites or cross-linking groups, e.g., RGD, in which the polymers retain their structural integrity while allowing for attachment of cells and molecules, such as proteins, nucleic acids, and the like.

Figure 2A:
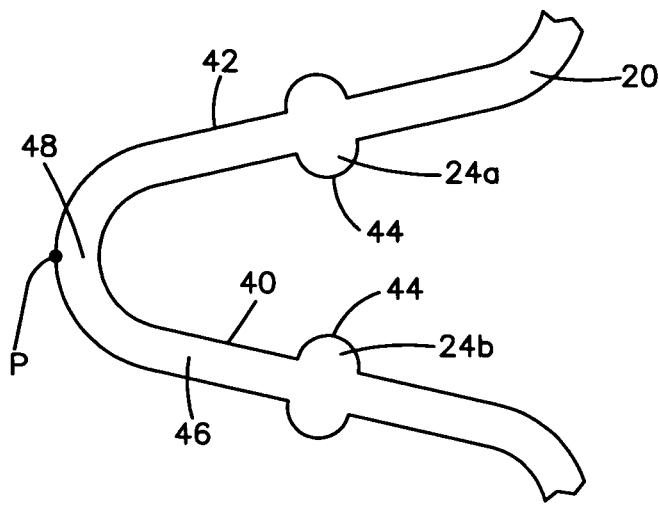
FIG. 2A is an enlarged view of an exemplary stent strut with web-inducing nodes in uncoated condition.

FIGS. 2A-2D show a strut 20 of an exemplary stent 10 having nodes 24, wherein the strut 20 goes from an uncoated condition (FIG. 2A), to a coated condition (FIG. 2B), to a compressed condition (FIG. 2C), to an expanded condition (FIG. 2D).

In these embodiments, strut 20 has an inner surface 40 and an outer surface 42. Strut 20 may also have a straight section 46 and a bent section 48. There may be a pivot point "P" located at or near the bent section 48. Strut 20 may also have at least one node 24. In these embodiments, strut 20 has at least two nodes 24a, 24b. A node 24 may have a node surface 44. As discussed in more detail below, nodes 24 may be of a variety of shapes and sizes. The nodes 24 in this embodiment are generally curved. Moreover, as discussed in more detail below, nodes 24 may be located in a variety of positions on a strut 20. In this embodiment, nodes 24a, 24b are located on the straight sections 46 of strut 20.

Figure 2B:
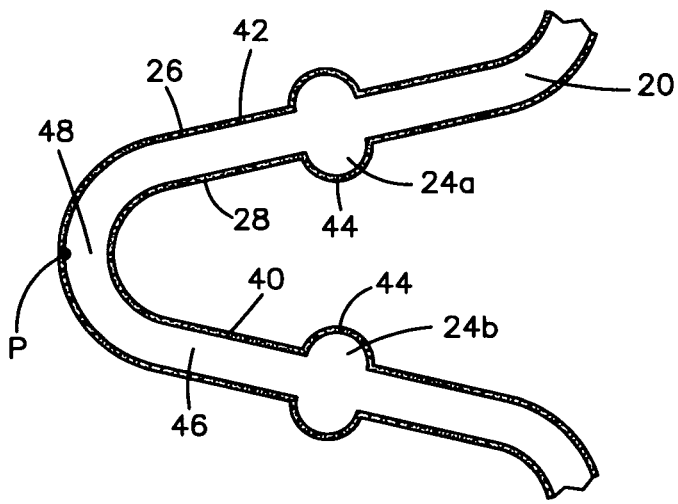
FIG. 2B shows the strut of FIG. 2A in a coated condition.

FIG. 2B shows the strut 20 of FIG. 2A after a coating 26 has been applied. Coating 26 may contain a therapeutic agent and/or a polymeric material. A more detailed discussion of coatings 26 appears below. The coating 26 may have an outer surface 28 after it is applied to a strut 20. Moreover, coating 26 may be applied to strut 20 in a variety of thicknesses, layers, and/or patterns. For instance, coating 26 may be applied to only one of the inner 40 or outer surface 42 of the strut 20. Coating 26 may be applied only to the nodes 24. Coating 26 may be applied thicker at or near the nodes 24. Coating 26 may be applied in a single layer, or in multiple layers.

FIG. 2C shows the strut 20 of FIG. 2B in a compressed condition. Strut 20 has been compressed, directionally shown by arrows, around pivot point P. FIG. 2C generally relates to a strut 20 that is part of a stent 10 that has been compressed or collapsed prior to insertion into a patient. In this embodiment, nodes 24a, 24b have been brought closer together such that the outer surfaces 28 of coating 26 on each node 24a, 24b are in contact. It may be preferable to compress strut 20 such that the outer surfaces 44 of the nodes 24a, 24b themselves are in contact. Also, the stent may be compressed so that the node of the first strut contacts an area of the second strut without a node.

FIG. 2D shows the strut 20 of FIG. 2C in an expanded condition. Strut 20 has been expanded, directionally shown by arrows, around pivot point P. One of skill in the art is aware of techniques for expanding the stent, such as using a balloon. FIG. 2D generally relates to a strut 20 that is part of a stent 10 that has been expanded after being introduced to a body lumen and/or a desired body tissue for treatment. In this embodiment, a web 30 of coating 26 has been formed generally between nodes 24a, 24b. Web 30 may be of varying size, shape, and thickness, and generally may be comprised of coating 26. The characteristics of a web 30 may be varied by such variables as the amount of coating 26 on the nodes 24, the shape, size, and/or location of the nodes 24, the amount of compression of the strut 20, and the amount of expansion of the strut 20.

Figure 2E:
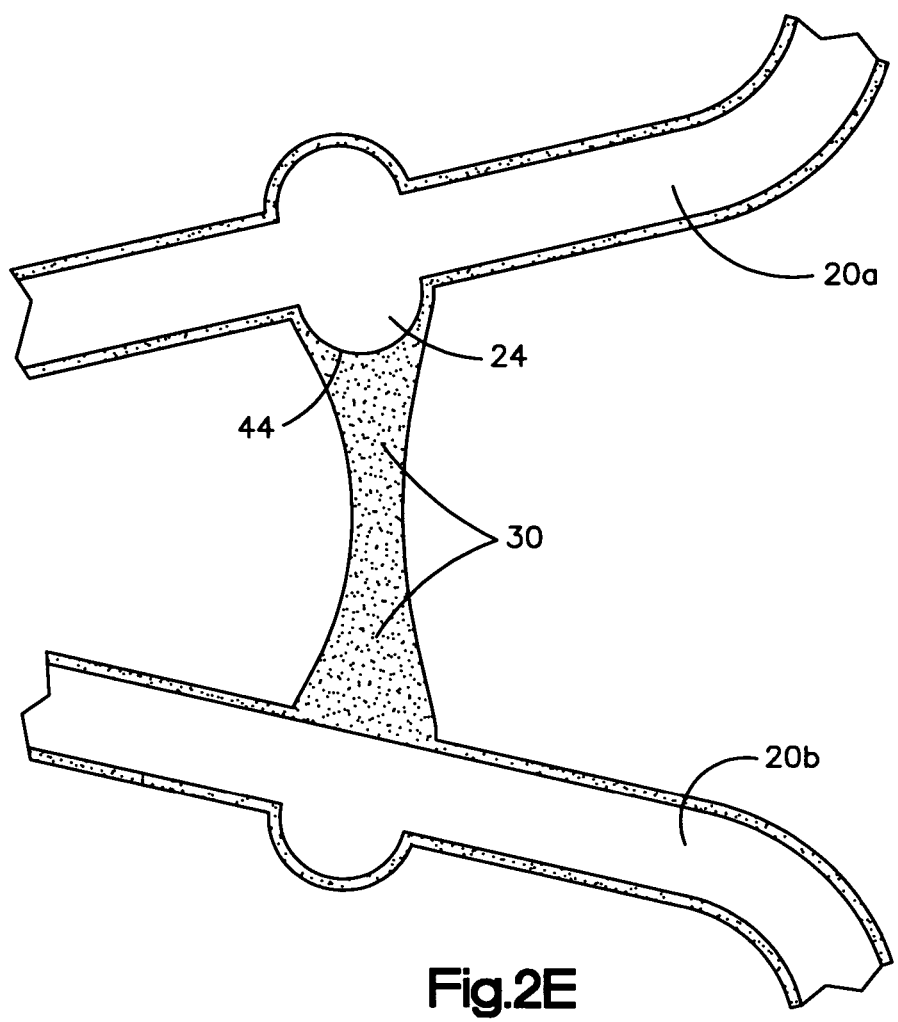
FIG. 2E shows an embodiment of two struts in an expanded condition, with a resulting web

FIG. 2E shows another embodiment where a web of coating material or composition can span two adjacent struts. In this embodiment, the first strut 20a has a node 24. The web 30 spans from the node 24 to a portion of a second strut 20b. The embodiments shown herein in which the web spans between portions of a strut can be modified accordingly so that the web in such embodiments can form between a first and second strut.

Webs 30 may be beneficial to deliver increased amounts of therapeutic material by way of increased drug elution area. As webs 30 may be comprised of coating 26, which may contain at least one therapeutic agent, webs 30 may serve as a "phantom strut" capable of delivering a therapeutic agent to a body site. Particularly advantageous, however, is that webs 30 may combine increased drug elution capabilities without adversely effecting the compression and expansion functions of the stent 10 and struts 20. Often, attempts to increases the therapeutic carrying capacity of a stent result in sacrificing the expansive qualities of a stent and/or strut, which may drastically reduce the effectiveness and/or safety of the device. Webs 30 may therefore provide a way to increase the therapeutic capacity of a stent 10 without adding more struts 20, and without creating undue traction between struts 20 when expanding from a compressed position.

It is may be preferable however, that webs 30 do not tear upon the expansion of the stent 10. To guard against the tearing of webs 30, the amount and properties of the coating 26 at nodes 24 may be varied such that a suitable amount of coating forms a web 30 that both resists tearing and still allows stent 10 to expand properly. Suitable materials for coating 26 may include a co-adhesive material, or polymers in general that have good elastomeric and/or co-adhesive properties. A detailed discussion of materials for coatings 26 appears below.

A UV-activated polymer may also be beneficial to prevent recoil of a stent 10 after expansion. UV (ultra-violet)-activated polymers are materials which change their mechanical properties upon exposure to UV light. Exposure to UV light causes these materials to polymerize, resulting in increased hardness and mechanical strength. In one embodiment, UV-activated polymer may be applied to the nodes 24. When the stent 10 is deployed, webs 30 of the UV-activated material may be formed. If UV light is now applied to the webs 30, the webs 30 may become hard, thus substantially increasing the radial compression resistance of the stent 10. This is an important property, as it may enable the development of flexible stents 10 for ease of delivery to the vasculature, which when deployed can be exposed to UV light thus imparting a high radial compression resistance to the stent 10.

A number of factors may contribute to the size, shape, volume, and other characteristics of a web 30, including but not limited to, the size, shape, volume, and surface characteristics of a node 24, the amount of coating 26 on a node 24, the rate and amount of expansion of a stent 10, the qualities of the coating 26 applied to the stent 10, the number of nodes 24 on a strut 20, the shape and flexibility of a strut 20, the interaction of nodes 24 and general geometry of the interaction with a node 24, and the amount of struts 20 in a stent 10. It may also be preferable to add bonus amounts of coating 26 to the nodes 24. This may be done after a stent 10 is coated with coating 26, and with a syringe to provide droplets of coating 26 to nodes 24, or other methods of material deposition which are known by those skilled in the art.

Figure 3A:
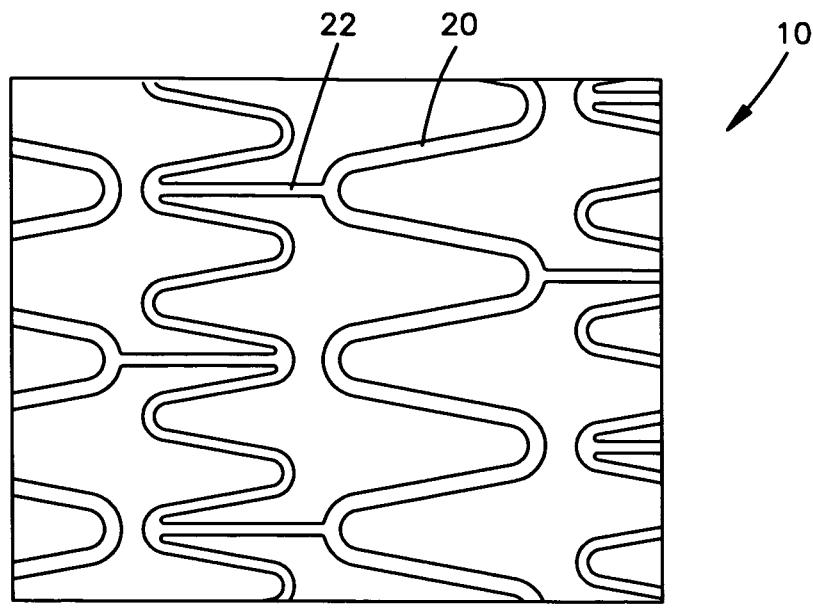
FIG. 3A is partial enlarged side view of an exemplary stent in an expanded state.
Figure 3B:
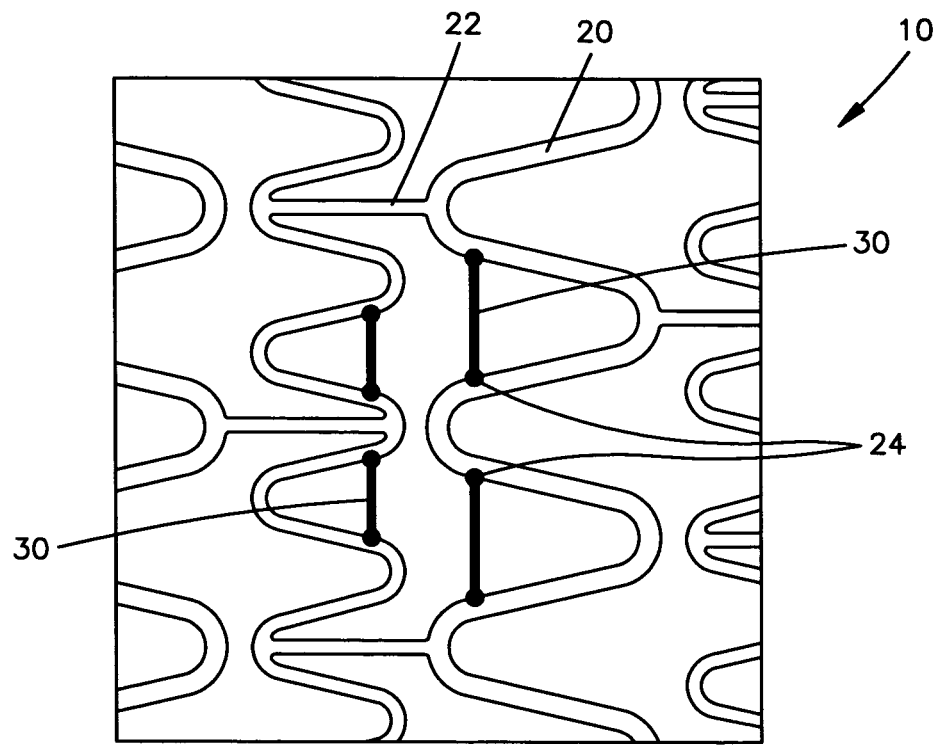
FIG. 3B shows the stent of FIG. 3A with webs.

FIGS. 3A-3B show a comparison of a stent 10 with struts 20, wherein one stent 10 is devoid of webs 30 (FIG. 3A) and another stent 10 that includes webs 30 between struts 20 (FIG. 3B). It is not difficult to appreciate that webs 30, especially in large numbers and/or in series, can noticeably increase the therapeutic elution area of a stent 10. Moreover, it may be preferable to arrange webs 30 in such a way that patterns are produced across a portion of a stent 10. Such patterns may elicit a more dispersed and even drug elution area across a portion of a stent 10.

FIGS. 4A-4K show various embodiments of struts 20 with at least one node 24 and a web 30. The variations of nodes 24 and webs 30 described herein are exemplary. It is expressly contemplated that those skilled in the art will appreciate that further variations in the spirit of the present invention are also attainable and/or preferable, depending on the desired use and materials. Each of the below described nodes 24 may appear at various locations on a strut 20, and in various sizes, with or without a coating 26.

Figure 4A:
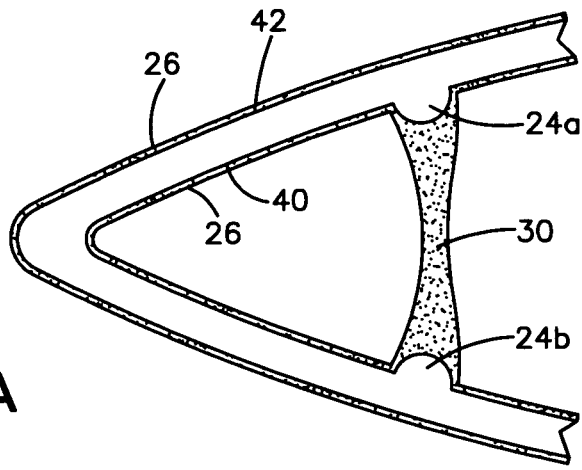
FIGS. 4A-4K show various embodiments of stent struts with a web of coating material.

FIG. 4A shows a strut 20 with two nodes 24a, 24b that are both of generally rounded shape, and a web 30 therebetween. Such a rounded shape may be circular, ovular, elliptical, or irregular. Nodes 24a, 24b are on the inner surface 40 of the strut 20. The strut 20 has a coating 26 disposed on both the inner 40 and outer surfaces 42 of the strut 20.

Figure 4B:
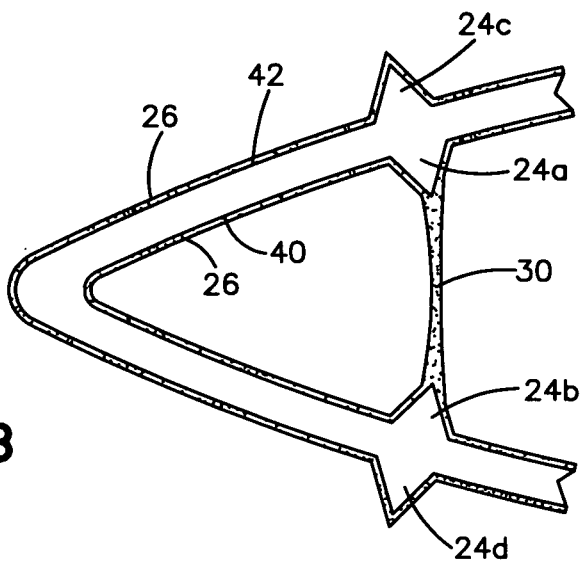

FIG. 4B shows a strut 20 with nodes 24a, 24b, 24c, 24d that are all of generally triangular shape, with a web 30 extending between nodes 24a and 24b. From a three-dimensional perspective, such a triangular shape may be pyramidal, polygonal, or irregular. Nodes 24a, 24b are on the inner surface 40, while nodes 24c, 24d are on the outer surface 42 of the strut 20. Again, coating 26 is disposed on the inner 40 and outer surfaces 42. However, the coating can be disposed on only the node or other selected portions of the stent.

Figure 4C:
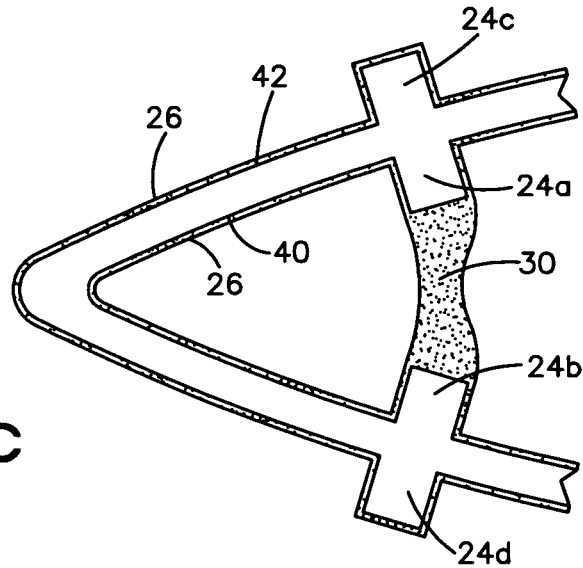

FIG. 4C is similar to the embodiment of FIG. 4B, except that nodes 24a-24d are substantially rectangular. Such a rectangular shape may be a square, rhombus, parallelogram, polygonal, or irregular.

Figure 4D:
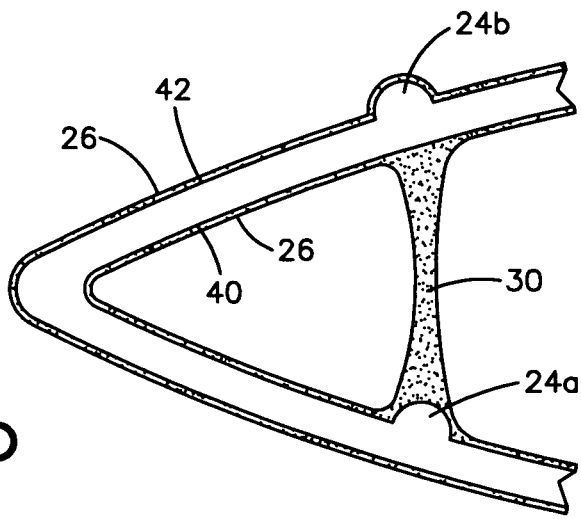

FIG. 4D shows a strut 20 with nodes 24a, 24b, wherein a web 30 extends between node 24a and inner surface without a node 40 located across the strut 20 from node 24a. Such a web 30 may be substantially similar to a web 30 formed between two nodes 24. Node 24b is located on the outer surface 42 of the strut 20. Coating 26 is disposed on both the inner 40 and outer surfaces 42.

Figure 4E:
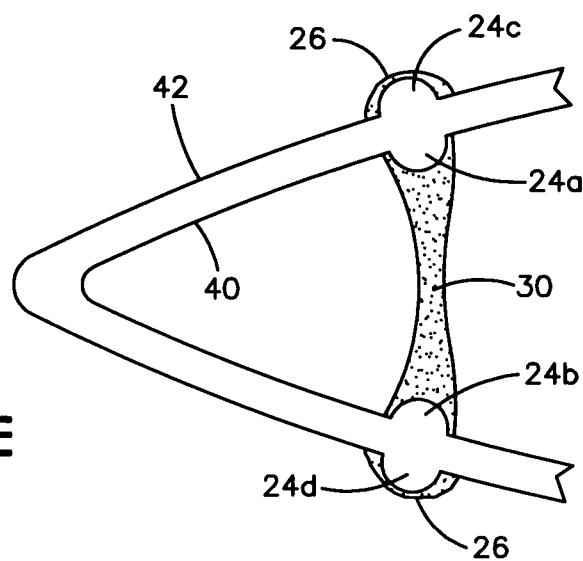

FIG. 4E shows a strut 20 with nodes 24a-24d, with a web 30 extending between nodes 24a, 24b. In this embodiment, both inner 40 and outer surfaces 42 are applied with a coating 26, but only at or near the nodes 24a-24d. This coating arrangement may be preferable if it is desired that the primary therapeutic delivery sites on a stent 10 be the webs 30 themselves.

Figure 4F:
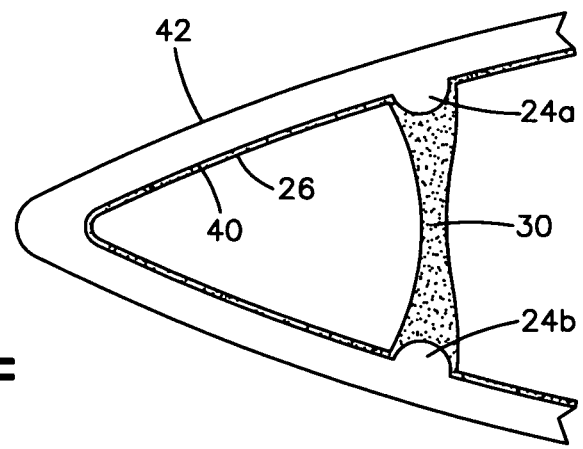

FIG. 4F shows another coating arrangement, wherein a strut 20 comprises nodes 24a, 24b and web extending therebetween. However, coating 26 is only applied to the inner surface 40 of strut in this embodiment, and not the outer surface 42.

Figure 4G:
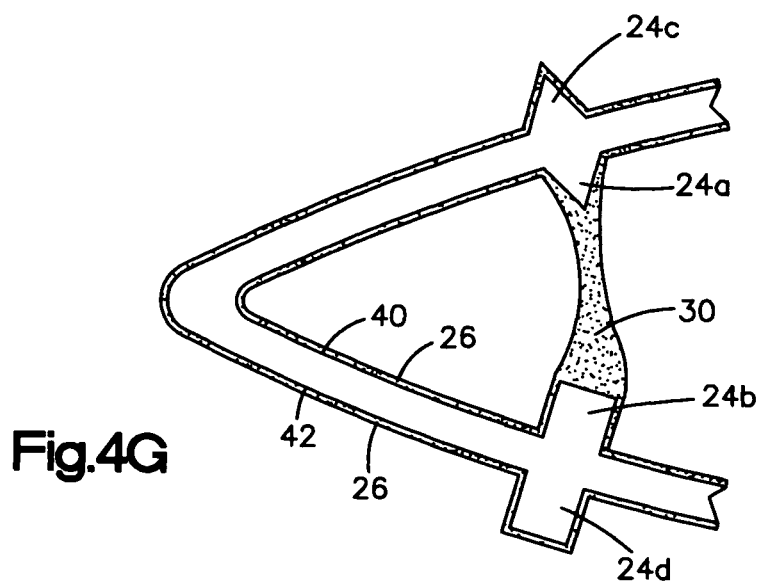
Figure 4H:
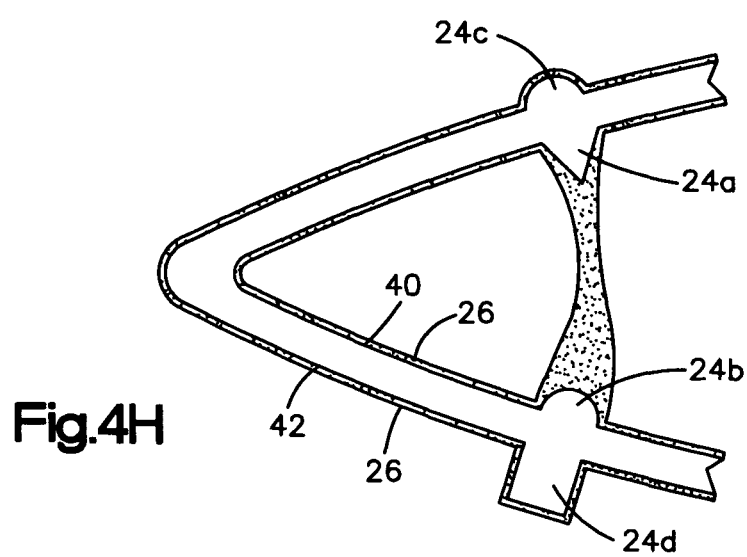

FIGS. 4G-4H show embodiments of struts 20 with nodes 24a-24d, wherein the nodes are a variety of shapes, and webs 30 formed between nodes 24a, 24b have irregular shapes at least in part based on the different shapes of nodes 24a, 24b. In these embodiments, coating 26 is disposed the inner 40 and outer surfaces 42.

Figure 4I:
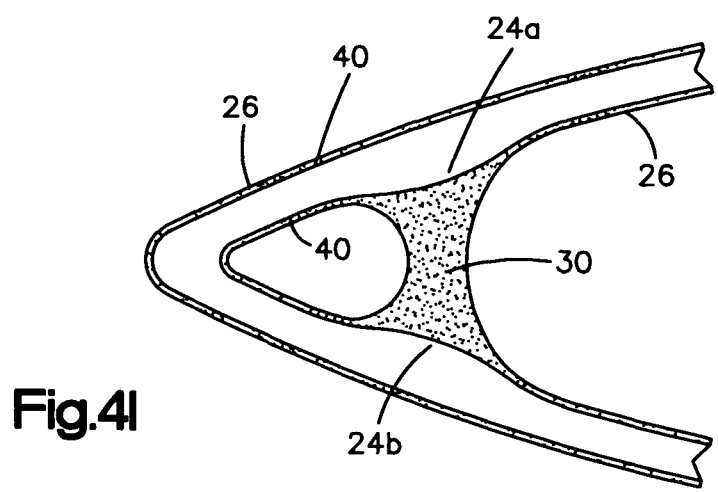

FIG. 4I shows a strut 20 with nodes 24a, 24b, and a web 30 extending therebetween. In this embodiment, nodes 24a, 24b are more subtle and less pronounced from the inner surface 40 of the strut 20, and may appear as bulges along the strut 20. Such a design may be beneficial to create a larger web 30, and to preserve more of the compressive features of the stent 10.

Figure 4J:
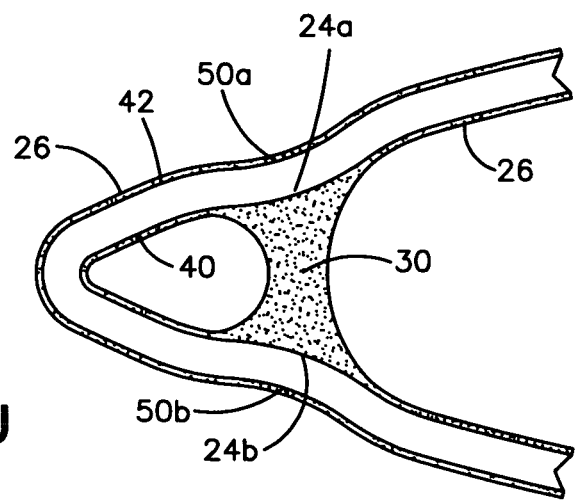

FIG. 4J shows an arrangement similar to the one of FIG. 4I, wherein the outer surface 42 of strut 20 have anti-nodes 50a, 50b located approximately adjacent nodes 24a, 24b on the inner surface 40 of the strut 20. Anti-nodes 50a, 50b may resemble depressions or undulations in the outer surface 42 of the strut 20. Anti-nodes may also appear on the inner surface 40, and may or may not have coating 26.

Figure 4K:
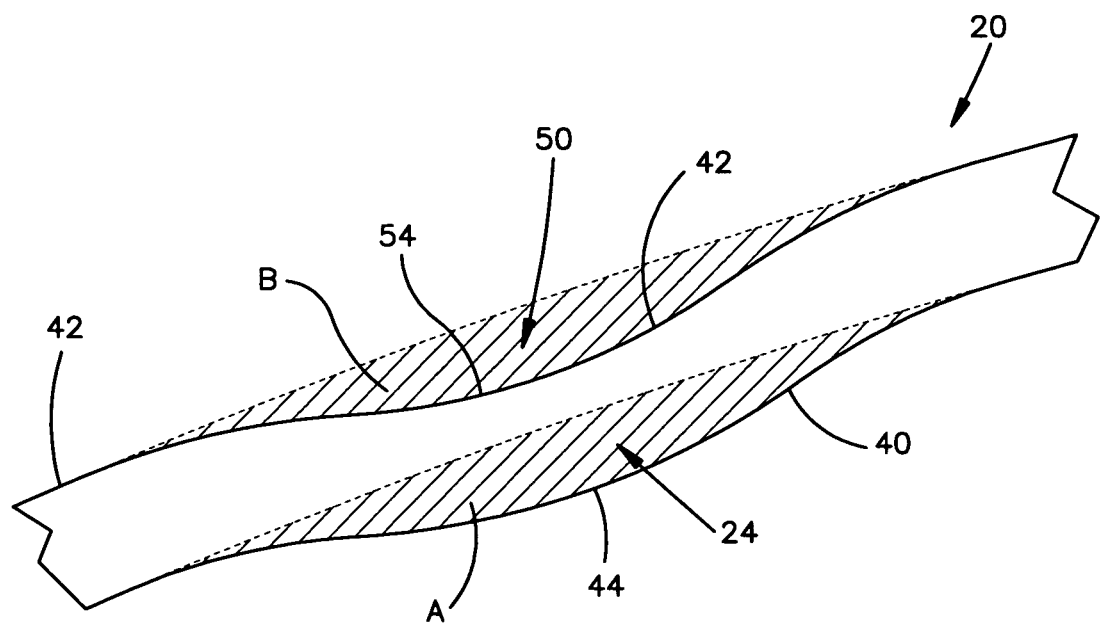

FIG. 4K shows an enlarged view of a node 24 and anti-node 50 substantially aligned on a strut 20. The dashed lines along the inner 40 and outer surfaces 42 of the strut indicate the variation of each surface with the presence of a node 24, and anti-node 50, respectively. The shaded portion "A" along the inner surface 40 indicates the cross-sectional area of node 24 from this perspective. Similarly, shaded portion "B" along the outer surface 42 indicates the cross-sectional area of anti-node 50 from this perspective. It may be preferable to create node 24 and anti-node 50 such that shaded areas A and B are approximately equal in size. Similarly, it may be preferable to align a node 24 with an anti-node 50. Moreover, it may be preferable to create node 24 and anti-node such that each are approximately the same volume. It may further be preferable to have more than one anti-node 50 on a single strut 20. Anti-node 50 may have an anti-node surface 54.

FIGS. 5A-5H also show various embodiments of struts 20 with at least one node 24 and at least one web 30. The variations of nodes 24 and webs 30 described herein again are exemplary. It is expressly contemplated that those skilled in the art will appreciate that further variations in the spirit of the present invention are also attainable and/or preferable, depending on the desired use and materials. Each of the below described nodes 24 may appear at various locations on a strut 20, and in various sizes, with or without a coating 26.

Figure 5A:
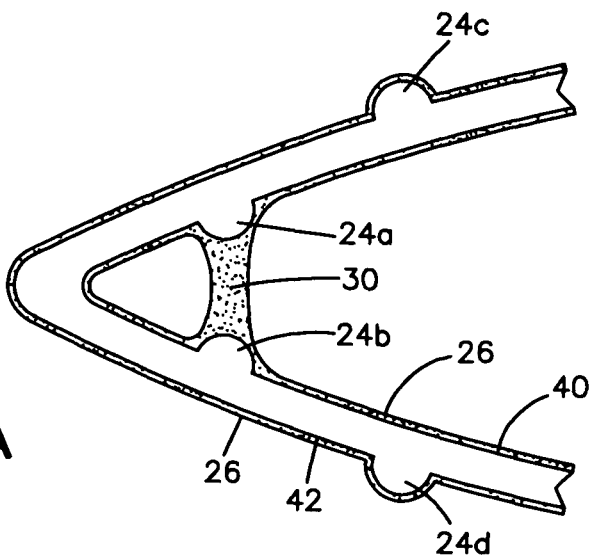
FIGS. 5A-5H show various embodiments of stent struts with at least one web of coating material.

FIG. 5A shows a strut 20 having nodes 24a, 24b, 24c, 24d, wherein a web 30 extends between nodes 24a, 24b. In this embodiment, nodes 24a, 24b are located on the inner surface 40 of the strut 20, and nodes 24c, 24d are located as a spaced-apart location on the outer surface 42. The distance between pairs of nodes 24a, 24b and 24c, 24d may be varied. Coating 26 is disposed on both the inner 40 and outer surfaces 42.

Figure 5B:
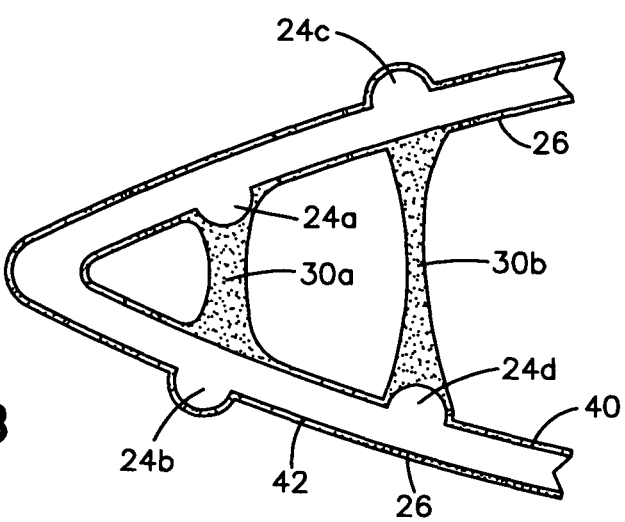

FIG. 5B shows a similar arrangement to that of FIG. 5A, except that in this embodiment, node 24b is located on the outer surface 42 of the strut 20, and node 24d is located on the inner surface 40. The result is that two webs 30a, 30b are formed between portions of the strut 20. It may be preferable to have more than two webs 30. Coating 26 is disposed on both the inner 40 and outer surfaces 42.

Figure 5C:
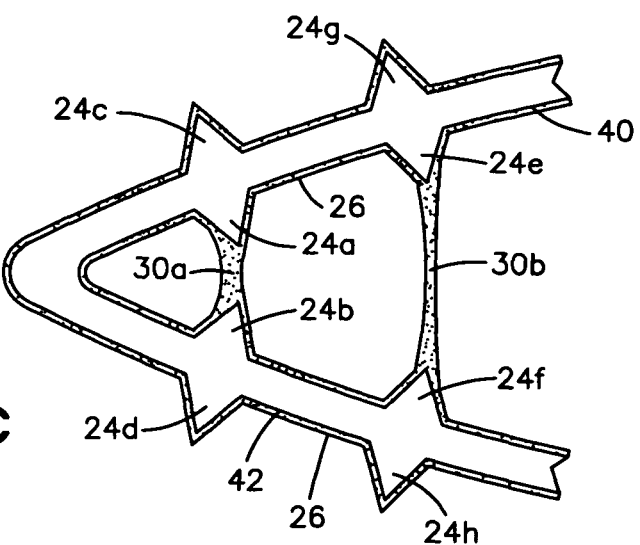

FIG. 5C shows a strut with nodes 24a-24h, wherein a web 30a extends between nodes 24a, 24b, and a web 30b extends between nodes 24e, 24f. All nodes 24a-24h in this embodiment are substantially triangular-shaped. Again, coating 26 is disposed on both the inner 40 and outer surfaces 42.

Figure 5D:
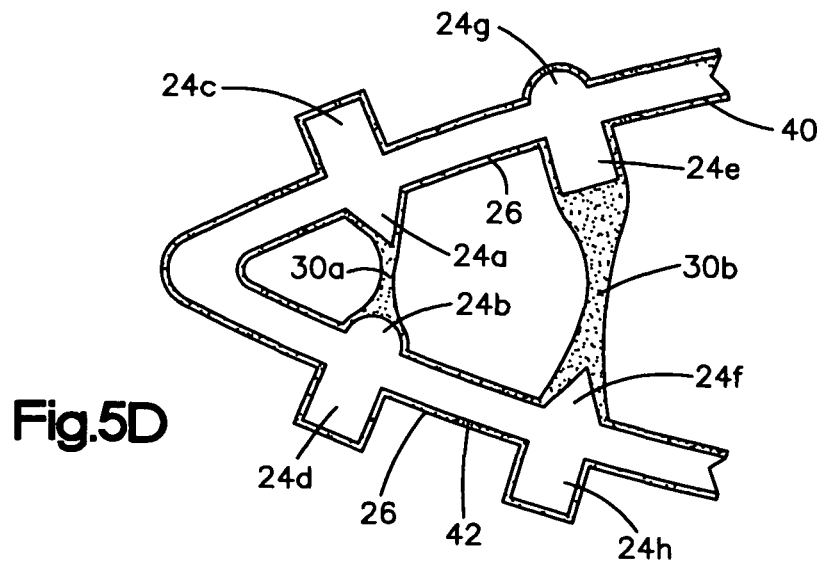

FIG. 5D combines the teachings of FIGS. 4G-4H and 5C to form a strut 20 with two webs 30a, 30b extending between nodes of different shapes. In this embodiment, nodes 24a, 24d, and 24f are triangular, nodes 24b and 24g are rounded, and nodes 24c, 24e, and 24h are rectangular. Other combinations of node 24 shapes are contemplated as well.

Figure 5E:
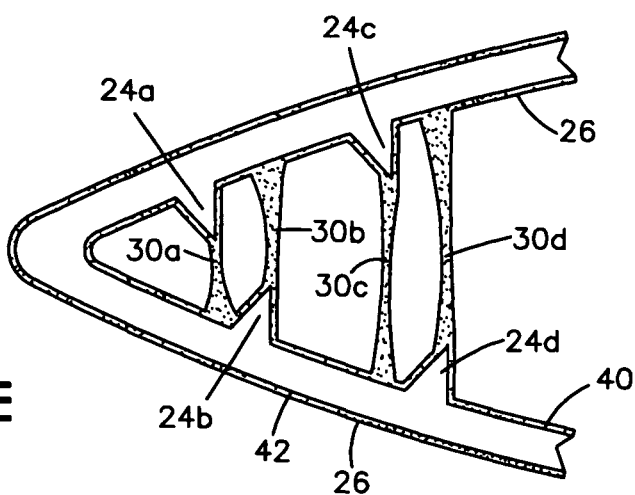

FIG. 5E shows a strut 20 with offset nodes 24a-24d located along the inner surface 40 of strut 20, with webs 30a-30d extending from each node to a corresponding location on the inner surface 40. The nodes 24a-24d in this embodiment are triangular, but may be of any suitable shape. The nodes 24a-24d are shaped, sized, and located in such a manner that webs 30 will not be formed from node-to-node.

Figure 5F:
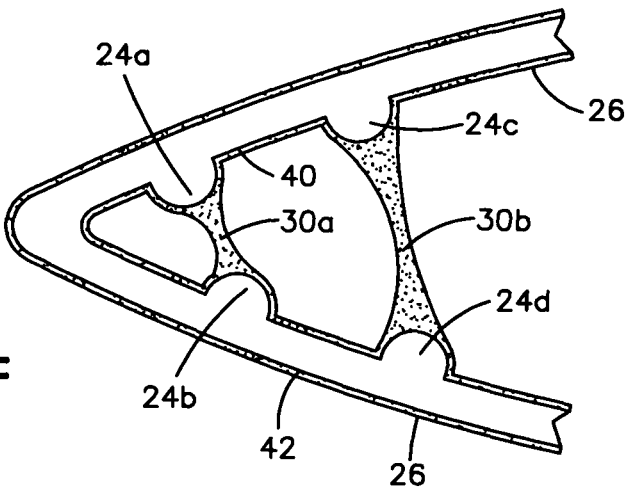

FIG. 5F shows a variation of the embodiment of FIG. 5E, wherein nodes 24a-24d are offset along the inner surface 40, but because of the shape, size, and/or location of the nodes 24a-24d, only two webs 30a, 30b are formed. Web 30a is formed between nodes 24a, 24b, and web 30b is formed between nodes 24c, 24d. However, because of the offset nature of the nodes 24a-24d, the webs 30a, 30b are slanted.

Figure 5G:
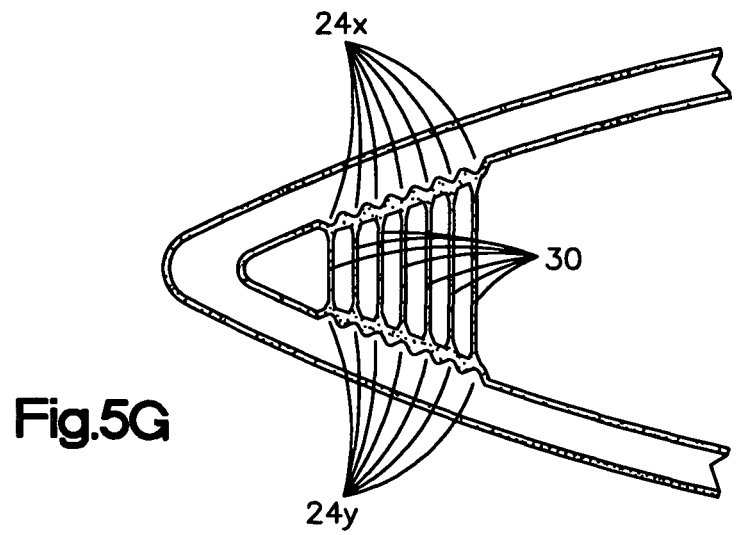
Figure 5H:
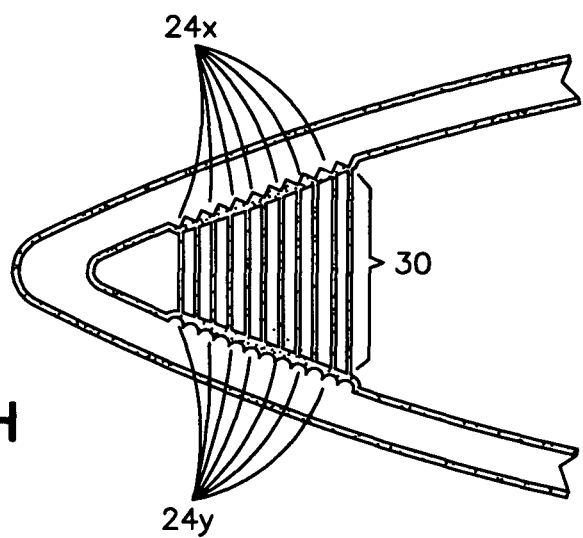

FIGS. 5G-5H are embodiments of a strut 20 having a series or plurality of nodes 24x, 24y located along the inner surface 40 of the strut 20, wherein a series of webs 30 are formed therebetween. Node series 24x, 24y may be formed as ridges (FIG. 5G), teeth (FIG. 5H, 24x), and/or bumps (FIG. 5H, 24y). Other shapes are contemplated as well, and combinations thereof. These arrangements may be beneficial to produce a series of thin webs 30 along a stretch of the strut 20. However, it is likely preferable that when series of nodes 24x, 24y are used, that the peaks of the individual nodes 24 align, and/or the series 24x, 24y are arranged so that they may not fit together in a peak-and-valley arrangement when the stent 10 is in a compressed position.

Nodes 24 may be formed in a variety of ways, including laser-cutting a strut to a predefined pattern including nodes 24. Nodes 24 may also be formed by chemical etching, or alternative material deposition methods which enable a node 24 to be added to a stent 10 after the stent 10 pattern has been cut.

As discussed above, it may be beneficial to apply a coating 26 to a stent 10 having struts 20. A coating composition may be prepared, for example, by applying a mixture of a therapeutic agent, solvent and/or a polymeric material on a surface to form a coating. If such a composition is used which includes a polymeric material, the polymeric material generally incorporates the therapeutic agent. Alternatively, the coating composition may not include a polymeric material. The following is a description of suitable materials and methods useful in producing a coating on the surface of stent struts of the invention.

Polymeric materials useful for forming the coating should be ones that are biocompatible, particularly during insertion or implantation of the device into the body and avoids irritation to body tissue. Examples of such polymers include, but not limited to, polyurethanes, polyisobutylene and its copolymers, silicones, and polyesters. Other suitable polymers include polyolefins, polyisobutylene, ethylene-alphaolefin copolymers, acrylic polymers and copolymers, vinyl halide polymers and copolymers such as polyvinyl chloride, polyvinyl ethers such as polyvinyl methyl ether, polyvinylidene halides such as polyvinylidene fluoride and polyvinylidene chloride, polyacrylonitrile, polyvinyl ketones, polyvinyl aromatics such as polystyrene, polyvinyl esters such as polyvinyl acetate; copolymers of vinyl monomers, copolymers of vinyl monomers and olefins such as ethylene-methyl methacrylate copolymers, acrylonitrile-styrene copolymers, ABS resins, ethylene-vinyl acetate copolymers, polyamides such as Nylon 66 and polycaprolactone, alkyd resins, polycarbonates, polyoxyethylenes, polyimides, polyethers, epoxy resins, polyurethanes, rayon-triacetate, cellulose, cellulose acetate, cellulose butyrate, cellulose acetate butyrate, cellophane, cellulose nitrate, cellulose propionate, cellulose ethers, carboxymethyl cellulose, collagens, chitins, polylactic acid, polyglycolic acid, and polylactic acid-polyethylene oxide copolymers. Since the polymer is being applied to a part of the medical device which undergoes mechanical challenges, e.g. expansion and contraction, the polymers are preferably selected from elastomeric polymers such as silicones (e.g. polysiloxanes and substituted polysiloxanes), polyurethanes, thermoplastic elastomers, ethylene vinyl acetate copolymers, polyolefin elastomers, and EPDM rubbers. The polymer is selected to allow the coating to better adhere to the surface of the strut when the stent is subjected to forces or stress. Furthermore, although the coating can be formed by using a single type of polymer, various combinations of polymers can be employed.

Generally, when a biologically active material used is a hydrophilic, e.g., heparin, then a matrix material comprising a more hydrophilic material has a greater affinity for the biologically active material than another matrix material that is less hydrophilic. When a biologically active material used is a hydrophobic, e.g., paclitaxel, actinomycin, sirolimus (RAPAMYCIN), tacrolimus, everolimus, and dexamethasone, then a matrix material that is more hydrophobic has a greater affinity for the biologically active material than another matrix material that is less hydrophobic.

Examples of suitable hydrophobic polymers include, but not limited to, polyolefins, such as polyethylene, polypropylene, poly(1-butene), poly(2-butene), poly(1-pentene), poly(2-pentene), poly(3-methyl-1-pentene), poly(4-methyl-1-pentene), poly(isoprene), poly(4-methyl-1-pentene), ethylene-propylene copolymers, ethylene-propylene-hexadiene copolymers, ethylene-vinyl acetate copolymers, blends of two or more polyolefins and random and block copolymers prepared from two or more different unsaturated monomers; styrene polymers, such as poly(styrene), poly(2-methylstyrene), styrene-acrylonitrile copolymers having less than about 20 mole-percent acrylonitrile, and styrene-2,2,3,3-tetrafluoropropyl methacrylate copolymers; halogenated hydrocarbon polymers, such as poly(chlorotrifluoroethylene), chlorotrifluoroethylene-tetrafluoroethylene copolymers, poly(hexafluoropropylene), poly(tetrafluoroethylene), tetrafluoroethylene, tetrafluoroethylene-ethylene copolymers, poly(trifluoroethylene), poly(vinyl fluoride), and poly(vinylidene fluoride); vinyl polymers, such as poly(vinyl butyrate), poly(vinyl decanoate), poly(vinyl dodecanoate), poly(vinyl hexadecanoate), poly(vinyl hexanoate), poly(vinyl propionate), poly(vinyl octanoate), poly(heptafluoroisopropoxyethylene), poly(heptafluoroisopropoxypropylene), and poly(methacrylonitrile); acrylic polymers, such as poly(n-butyl acetate), poly(ethyl acrylate), poly(1-chlorodifluoromethyl)tetrafluoroethyl acrylate, poly di(chlorofluoromethyl)fluoromethyl acrylate, poly(1,1-dihydroheptafluorobutyl acrylate), poly(1,1-dihydropentafluoroisopropyl acrylate), poly(1,1-dihydropentadecafluorooctyl acrylate), poly(heptafluoroisopropyl acrylate), poly 5-(heptafluoroisopropoxy)pentyl acrylate, poly 11-(heptafluoroisopropoxy)undecyl acrylate, poly 2-(heptafluoropropoxy)ethyl acrylate, and poly(nonafluoroisobutyl acrylate); methacrylic polymers, such as poly(benzyl methacrylate), poly(n-butyl methacrylate), poly(isobutyl methacrylate), poly(t-butyl methacrylate), poly(t-butylaminoethyl methacrylate), poly(dodecyl methacrylate), poly(ethyl methacrylate), poly(2-ethylhexyl methacrylate), poly(n-hexyl methacrylate), poly(phenyl methacrylate), poly(n-propyl methacrylate), poly(octadecyl methacrylate), poly(1,1-dihydropentadecafluorooctyl methacrylate), poly(heptafluoroisopropyl methacrylate), poly(heptadecafluorooctyl methacrylate), poly(1-hydrotetrafluoroethyl methacrylate), poly(1,1-dihydrotetrafluoropropyl methacrylate), poly(1-hydrohexafluoroisopropyl methacrylate), and poly(t-nonafluorobutyl methacrylate); polyesters, such a poly (ethylene terephthalate) and poly(butylene terephthalate); condensation type polymers such as and polyurethanes and siloxane-urethane copolymers; polyorganosiloxanes, i.e., polymeric materials characterized by repeating siloxane groups, represented by $R_a SiO_{4-a/2}$, where R is a monovalent substituted or unsubstituted hydrocarbon radical and the value of a is 1 or 2; and naturally occurring hydrophobic polymers such as rubber.

Examples of suitable hydrophilic monomer include, but not limited to; (meth)acrylic acid, or alkaline metal or ammonium salts thereof; (meth)acrylamide; (meth)acrylonitrile; those polymers to which unsaturated dibasic, such as maleic acid and fumaric acid or half esters of these unsaturated dibasic acids, or alkaline metal or ammonium salts of these dibasic adds or half esters, is added; those polymers to which unsaturated sulfonic, such as 2-acrylamido-2-methylpropanesulfonic, 2-(meth)acryloylethanesulfonic acid, or alkaline metal or ammonium salts thereof, is added; and 2-hydroxyethyl(meth)acrylate and 2-hydroxypropyl(meth)acrylate.

Polyvinyl alcohol is also an example of hydrophilic polymer. Polyvinyl alcohol may contain a plurality of hydrophilic groups such as hydroxyl, amido, carboxyl, amino, ammonium or sulfonyl ($-SO_3$). Hydrophilic polymers also include, but are not limited to, starch, polysaccharides and related cellulosic polymers; polyalkylene glycols and oxides such as the polyethylene oxides; polymerized ethylenically unsaturated carboxylic acids such as acrylic, mathacrylic and maleic acids and partial esters derived from these acids and polyhydric alcohols such as the alkylene glycols; homopolymers and copolymers derived from acrylamide; and homopolymers and copolymers of vinylpyrrolidone.

The term "therapeutic agent" as used in the present invention encompasses drugs, genetic materials, and biological materials and can be used interchangeably with "biologically active material". Non-limiting examples of suitable therapeutic agent include heparin, heparin derivatives, urokinase, dextrophenylalanine proline arginine chloromethylketone (PPack), enoxaprin, angiopeptin, hirudin, acetylsalicylic acid, tacrolimus, everolimus, rapamycin (sirolimus), pimecrolimus, amlodipine, doxazosin, glucocorticoids, betamethasone, dexamethasone, prednisolone, corticosterone, budesonide, sulfasalazine, rosiglitazone, mycophenolic acid, mesalamine, paclitaxel, 5-fluorouracil, cisplatin, vinblastine, vincristine, epothilones, methotrexate, azathioprine, adriamycin, mutamycin, endostatin, angiostatin, thymidine kinase inhibitors, cladribine, lidocaine, bupivacaine, ropivacaine, D-Phe-Pro-Arg chloromethyl ketone, platelet receptor antagonists, anti-thrombin antibodies, anti-platelet receptor antibodies, aspirin, dipyridamole, protamine, hirudin, prostaglandin inhibitors, platelet inhibitors, trapidil, liprostin, tick antiplatelet peptides, 5-azacytidine, vascular endothelial growth factors, growth factor receptors, transcriptional activators, translational promoters, antiproliferative agents, growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin, cholesterol lowering agents, vasodilating agents, agents which interfere with endogenous vasoactive mechanisms, antioxidants, probucol, antibiotic agents, penicillin, cefoxitin, oxacillin, tobranycin, angiogenic substances, fibroblast growth factors, estrogen, estradiol (E2), estriol (E3), 17-beta estradiol, digoxin, beta blockers, captopril, enalopril, statins, steroids, vitamins, paclitaxel (as well as its derivatives, analogs or paclitaxel bound to proteins, e.g. Abraxane™) 2'-succinyl-taxol, 2'-succinyl-taxol triethanolamine, 2'-glutaryl-taxol, 2'-glutaryl-taxol triethanolamine salt, 2'-O-ester with N-(dimethylaminoethyl)glutamine, 2'-O-ester with N-(dimethylaminoethyl) glutamide hydrochloride salt, nitroglycerin, nitrous oxides, nitric oxides, antibiotics, aspirins, digitalis, estrogen, estradiol and glycosides. In one embodiment, the therapeutic agent is a smooth muscle cell inhibitor or antibiotic. In a preferred embodiment, the therapeutic agent is taxol (e.g., Taxol®), or its analogs or derivatives. In another preferred embodiment, the therapeutic agent is paclitaxel, or its analogs or derivatives. In yet another preferred embodiment, the therapeutic agent is an antibiotic such as erythromycin, amphotericin, rapamycin, adriamycin, etc.

The term "genetic materials" means DNA or RNA, including, without limitation, of DNA/RNA encoding a useful protein stated below, intended to be inserted into a human body including viral vectors and non-viral vectors.

The term "biological materials" include cells, yeasts, bacteria, proteins, peptides, cytokines and hormones. Examples for peptides and proteins include vascular endothelial growth factor (VEGF), transforming growth factor (TGF), fibroblast growth factor (FGF), epidermal growth factor (EGF), cartilage growth factor (CGF), nerve growth factor (NGF), keratinocyte growth factor (KGF), skeletal growth factor (SGF), osteoblast-derived growth factor (BDGF), hepatocyte growth factor (HGF), insulin-like growth factor (IGF), cytokine growth factors (CGF), platelet-derived growth factor (PDGF), hypoxia inducible factor-1 (HIF-1), stem cell derived factor (SDF), stem cell factor (SCF), endothelial cell growth supplement (ECGS), granulocyte macrophage colony stimulating factor (GM-CSF), growth differentiation factor (GDF), integrin modulating factor (IMF), calmodulin (CaM), thymidine kinase (TK), tumor necrosis factor (TNF), growth hormone (GH), bone morphogenic protein (BMP) (e.g., BMP-2, BMP-3, BMP-4, BMP-5, BMP-6 (Vgr-1), BMP-7 (PO-1), BMP-8, BMP-9, BMP-10, BMP-11, BMP-12, BMP-14, BMP-15, BMP-16, etc.), matrix metalloproteinase (MMP), tissue inhibitor of matrix metalloproteinase (TIMP), cytokines, interleukin (e.g., IL-1, IL-2, IL-3, IL-4, IL-5, IL-6, IL-7, IL-8, IL-9, IL-10, IL-11, IL-12, IL-15, etc.), lymphokines, interferon, integrin, collagen (all types), elastin, fibrillins, fibronectin, vitronectin, laminin, glycosaminoglycans, proteoglycans, transferrin, cytotactin, cell binding domains (e.g., RGD), and tenascin. Currently preferred BMP's are BMP-2, BMP-3, BMP-4, BMP-5, BMP-6, BMP-7. These dimeric proteins can be provided as homodimers, heterodimers, or combinations thereof, alone or together with other molecules. Cells can be of human origin (autologous or allogeneic) or from an animal source (xenogeneic), genetically engineered, if desired, to deliver proteins of interest at the transplant site. The delivery media can be formulated as needed to maintain cell function and viability. Cells include progenitor cells (e.g., endothelial progenitor cells), stem cells (e.g., mesenchymal, hematopoietic, neuronal), stromal cells, parenchymal cells, undifferentiated cells, fibroblasts, macrophage, and satellite cells.

Other non-genetic therapeutic agents include:
anti-thrombogenic agents such as heparin, heparin derivatives, urokinase, and PPack (dextrophenylalanine proline arginine chloromethylketone);
anti-proliferative agents such as enoxaprin, angiopeptin, or monoclonal antibodies capable of blocking smooth muscle cell proliferation, hirudin, acetylsalicylic acid, tacrolimus, everolimus, amlodipine and doxazosin;
anti-inflammatory agents such as glucocorticoids, betamethasone, dexamethasone, prednisolone, corticosterone, budesonide, estrogen, sulfasalazine, rosiglitazone, mycophenolic acid and mesalamine;
anti-neoplastic/anti-proliferative/anti-miotic agents such as paclitaxel, 5-fluorouracil, cisplatin, vinblastine, vincristine, epothilones, methotrexate, azathioprine, adriamycin and mutamycin; endostatin, angiostatin and thymidine kinase inhibitors, cladribine, taxol and its analogs or derivatives;
anesthetic agents such as lidocaine, bupivacaine, and ropivacaine;
anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, aspirin (aspirin is also classified as an analgesic, antipyretic and anti-inflammatory drug), dipyridamole, protamine, hirudin, prostaglandin inhibitors, platelet inhibitors, antiplatelet agents such as trapidil or liprostin and tick antiplatelet peptides;
DNA demethylating drugs such as 5-azacytidine, which is also categorized as a RNA or DNA metabolite that inhibit cell growth and induce apoptosis in certain cancer cells;
vascular cell growth promoters such as growth factors, vascular endothelial growth factors (VEGF, all types including VEGF-2), growth factor receptors, transcriptional activators, and translational promoters;
vascular cell growth inhibitors such as anti-proliferative agents, growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin;
cholesterol-lowering agents, vasodilating agents, and agents which interfere with endogenous vasoactive mechanisms;
anti-oxidants, such as probucol;
antibiotic agents, such as penicillin, cefoxitin, oxacillin, tobranycin, rapamycin (sirolimus);
angiogenic substances, such as acidic and basic fibroblast growth factors, estrogen including estradiol (E2), estriol (E3) and 17-beta estradiol;
drugs for heart failure, such as digoxin, beta-blockers, angiotensin-converting enzyme (ACE) inhibitors including captopril and enalopril, statins and related compounds; and
macrolides such as sirolimus or everolimus.

Preferred biological materials include anti-proliferative drugs such as steroids, vitamins, and restenosis-inhibiting agents. Preferred restenosis-inhibiting agents include microtubule stabilizing agents such as Taxol®, paclitaxel (i.e., paclitaxel, paclitaxel analogs, or paclitaxel derivatives, and mixtures thereof). For example, derivatives suitable for use in the present invention include 2'-succinyl-taxol, 2'-succinyl-taxol triethanolamine, 2'-glutaryl-taxol, 2'-glutaryl-taxol triethanolamine salt, 2'-O-ester with N-(dimethylaminoethyl) glutamine, and 2'-O-ester with N-(dimethylaminoethyl) glutamide hydrochloride salt.

Other suitable therapeutic agents include tacrolimus; halofuginone; inhibitors of HSP90 heat shock proteins such as geldanamycin; microtubule stabilizing agents such as epothilone D; phosphodiesterase inhibitors such as cliostazole; Barkct inhibitors; phospholamban inhibitors; and Serca 2 gene/proteins.

Other preferred therapeutic agents include nitroglycerin, nitrous oxides, nitric oxides, aspirins, digitalis, estrogen derivatives such as estradiol and glycosides.

In one embodiment, the therapeutic agent is capable of altering the cellular metabolism or inhibiting a cell activity, such as protein synthesis, DNA synthesis, spindle fiber formation, cellular proliferation, cell migration, microtubule formation, microfilament formation, extracellular matrix synthesis, extracellular matrix secretion, or increase in cell volume. In another embodiment, the therapeutic agent is capable of inhibiting cell proliferation and/or migration.

In certain embodiments, the therapeutic agents for use in the medical devices of the present invention can be synthesized by methods well known to one skilled in the art. Alternatively, the therapeutic agents can be purchased from chemical and pharmaceutical companies.

The solvent that is used to form the coating composition include ones which can dissolve the polymer into solution and do not alter or adversely impact the therapeutic properties of the therapeutic agent employed. Examples of useful solvents include tetrahydrofuran (THF), methyl ethyl ketone chloroform, toluene, acetone, issoctane, 1,1,1-trichloroethane, isoppropanol, IPA and dichloromethane or mixtures thereof.

Suitable stents may also be coated or made with non-polymeric materials. Examples of useful non-polymeric materials include sterols such as cholesterol, stigmasterol, β-sitosterol, and estradiol; cholesteryl esters such as cholesteryl stearate; $C_{12}$-$C_{24}$ fatty acids such as lauric acid, myristic acid, palmitic acid, stearic acid, arachidic acid, behenic acid, and lignoceric acid; $C_{18}$-$C_{36}$ mono-, di- and triacylglycerides such as glyceryl monooleate, glyceryl monolinoleate, glyceryl monolaurate, glyceryl monodocosanoate, glyceryl monomyristate, glyceryl monodicenoate, glyceryl dipalmitate, glyceryl didocosanoate, glyceryl dimyristate, glyceryl didecenoate, glyceryl tridocosanoate, glyceryl trimyristate, glyceryl tridecenoate, glycerol tristearate and mixtures thereof; sucrose fatty acid esters such as sucrose distearate and sucrose palmitate; sorbitan fatty acid esters such as sorbitan monostearate, sorbitan monopalmitate and sorbitan tristearate; $C_{16}$-$C_{18}$ fatty alcohols such as cetyl alcohol, myristyl alcohol, stearyl alcohol, and cetostearyl alcohol; esters of fatty alcohols and fatty acids such as cetyl palmitate and cetearyl palmitate; anhydrides of fatty acids such as stearic anhydride; phospholipids including phosphatidylcholine (lecithin), phosphatidylserine, phosphatidylethanolamine, phosphatidylinositol, and lysoderivatives thereof; sphingosine and derivatives thereof; sphingomyelins such as stearyl, palmitoyl, and tricosanyl sphingomyelins; ceramides such as stearyl and palmitoyl ceramides; glycosphingolipids; lanolin and lanolin alcohols; and combinations and mixtures thereof. Preferred non-polymeric materials include cholesterol, glyceryl monostearate, glycerol tristearate, stearic acid, stearic anhydride, glyceryl monooleate, glyceryl monolinoleate, and acetylated monoglycerides.

In one method of forming the aforementioned coating layers, a coating material composition is applied to the surface. Coating compositions can be applied by any method to a surface of a medical device to form a coating layer. Examples of suitable methods include, but are not limited to, spraying such as by conventional nozzle or ultrasonic nozzle, dipping, rolling, electrostatic deposition, and a batch process such as air suspension, pan coating or ultrasonic mist spraying. Also, more than one coating method can be used to make a medical device. Coating compositions suitable for applying a coating to the devices of the present invention can include a polymeric material dispersed or dissolved in a solvent suitable for the medical device, wherein upon applying the coating composition to the medical device, the solvent is removed. Such systems are commonly known to the skilled artisan.

A coating of a medical device of the present invention may include multiple coating layers. For example, the first layer and the second layer may contain different biologically active materials. Alternatively, the first layer and the second layer may contain an identical biologically active material having different concentrations. In one embodiment, either of the first layer or the second layer may be free of biologically active material. For example, when the biologically active solution is applied onto a surface and dried (the first layer), a coating composition free of a biologically active material (the second layer) can be applied over the dried biologically active material.

The description contained herein is for purposes of illustration and not for purposes of limitation. Changes and modifications may be made to the embodiments of the description and still be within the scope of the invention. Furthermore, obvious changes, modifications or variations will occur to those skilled in the art. Also, all references cited above are incorporated herein by reference, in their entirety, for all purposes related to this disclosure.

While the invention has been shown and described herein with reference to particular embodiments, it is to be understood that the various additions, substitutions, or modifications of form, structure, arrangement, proportions, materials, and components and otherwise, used in the practice and which are particularly adapted to specific environments and operative requirements, may be made to the described embodiments without departing from the spirit and scope of the present invention. Accordingly, it should be understood that the embodiments disclosed herein are merely illustrative of the principles of the invention. Various other modifications may be made by those skilled in the art which will embody the principles of the invention and fall within the spirit and the scope thereof.

What is claimed is:

1. A medical device for delivering a therapeutic agent comprising:
   a tubular stent comprising a stent frame, the stent frame having a sidewall and a plurality of serpentine bands, each serpentine band having a plurality of circumferentially adjacent struts with openings therebetween, the struts including at least a first strut and a second strut circumferentially adjacent the first strut, wherein the first strut defines at least a first node on a first portion thereof and the second strut defines at least a second node on a second portion thereof, the second node circumferentially adjacent the first node,
   the stent having an unexpanded state and an expanded state, each node defining a protuberance extending from a side of the strut into one of the openings;
   a coating composition comprising a therapeutic agent disposed on the first and second nodes; and
   in the expanded state webs, the webs consisting of the coating composition, wherein the webs extend exclusively between circumferentially adjacent nodes of circumferentially adjacent struts of the same band, each web which extends between circumferentially adjacent nodes dividing the opening between circumferentially adjacent struts into at least two non-contiguous open spaces.

2. The device of claim 1, wherein the first node is substantially rounded.

3. The device of claim 1, wherein the first node is substantially triangular.

4. The device of claim 1, wherein the first node is substantially rectangular.

5. The device of claim 1, wherein the first node and the second node are substantially the same shape.

6. The device of claim 1, wherein the first node and the second node are substantially the same size.

7. The device of claim 1, wherein at least a portion of the stent is coated with a UV-activated polymer.

8. The device of claim 1, wherein the first portion comprises at least a third node, and the second portion comprises a fourth node; and wherein in the expanded state a first web extends between the first node and the second node, and in the expanded state a second web extends between the third node and the fourth node.

9. The device of claim 8, wherein the first web and the second web are different shapes.

10. The device of claim 8, wherein the first node and the second node are substantially a first shape, and wherein the third node and the fourth node are substantially a second shape, and wherein the first shape is substantially different than the second shape.

11. The device of claim 8, wherein the first node and the second node are substantially a first size, and wherein the third node and the fourth node are substantially a second size, and wherein the first size is larger than the second size.

12. The device of claim 1, wherein the first portion comprises a first plurality of nodes and the second portion comprises a second plurality of nodes; and wherein a plurality of webs extends between the first plurality of nodes and the second plurality of nodes.

13. A medical device for delivering a therapeutic agent comprising:
a tubular stent comprising a sidewall and a plurality of serpentine bands, each serpentine band having a plurality of circumferentially adjacent struts, the struts having an inner surface, an outer surface, and side surfaces extending between the inner and outer surfaces, the struts further defining openings between adjacent side surface, the struts including at least a first strut and a second strut circumferentially adjacent the first strut, wherein the first strut comprises a first node along a portion of one of the side surfaces and the second strut comprises a second node along a portion of one of the side surfaces circumferentially adjacent the first node, the stent having an unexpanded state and an expanded state;
a coating composition comprising a therapeutic agent disposed on the first and second nodes; and
in the expanded state, webs consisting of the coating composition, wherein the first node comprises a protuberance protruding laterally from the first strut into one of the openings and wherein the webs extend exclusively between circumferentially adjacent nodes of circumferentially adjacent struts of the same band and span only portions of the openings therebetween.

14. The device of claim 13, wherein the second strut comprises at least a second node, and wherein a first web extends between the first node and the second node.

15. The device of claim 13, wherein the first node is substantially rounded.

16. The device of claim 13, wherein the first node is substantially triangular.

17. The device of claim 13, wherein the first node is substantially rectangular.

18. The device of claim 14, wherein the first node and the second node are substantially the same shape.

19. The device of claim 14, wherein the first node and the second node are substantially the same size.

20. The device of claim 13, wherein at least a portion of the stent is coated with a UV-activated polymer.

21. The device of claim 13, wherein the first strut comprises at least a third node, and the second strut comprises a fourth node; and wherein a first web extends between the first node and the second node, and a second web extends between the third node and the fourth node.

22. The device of claim 21, wherein the first web and the second web are different shapes.

23. The device of claim 21, wherein the first node and the second node are substantially a first shape, and wherein the third node and the fourth node are substantially a second shape, and wherein the first shape is substantially different than the second shape.

24. The device of claim 21, wherein the first node and the second node are substantially a first size, and wherein the third node and the fourth node are substantially a second size, and wherein the first size is larger than the second size.

25. The device of claim 13, wherein the first strut comprises a first plurality of nodes and the second strut comprises a second plurality of nodes; and wherein a plurality of webs extends between the first plurality of nodes and the second plurality of nodes.

26. A medical device for delivering a therapeutic agent comprising:
a sidewall formed of a plurality of serpentine bands, each serpentine band comprising interconnected struts defining protuberances along portions thereof, the interconnected struts of each band being circumferentially adjacent to one another and defining openings therebetween, the protuberances extending into the openings, and the sidewall being expandable from a first configuration to a second, enlarged configuration;
a coating composition comprising a therapeutic agent; and
in the second, enlarged configuration, a plurality of strands consisting of the coating composition, each strand extending across at least a portion of one of said openings, the strands dividing said openings across which strands extend into at least two non-contiguous open spaces, the open spaces extending all the way through the sidewall, wherein the strands extend exclusively between circumferentially adjacent struts of the same band.

27. The stent of claim 26 wherein the strands extend from a protuberance on one strut to a protuberance on the adjacent strut.

28. The stent of claim 26 further comprising a first strand, wherein the first strand has a first end, a second end and a middle region therebetween, the first end emanating from a protuberance on one strut, the second end emanating from a protuberance on the adjacent strut, and the middle region being narrower than the first and second ends.

* * * * *